United States Patent [19]

Martino et al.

[11] Patent Number: 5,612,443

[45] Date of Patent: Mar. 18, 1997

[54] LOW MOLECULAR WEIGHT POLYALDEHYDES

[75] Inventors: Gary T. Martino, Plainsboro; Martin M. Tessler, Edison, both of N.J.

[73] Assignee: National Starch and Chemical Investment Holding Corporation, Wilmington, Del.

[21] Appl. No.: 460,289

[22] Filed: Jun. 2, 1995

Related U.S. Application Data

[62] Division of Ser. No. 310,451, Sep. 22, 1994, Pat. No. 5,466,862, which is a division of Ser. No. 74,278, Jun. 8, 1993, Pat. No. 5,386,040, which is a continuation of Ser. No. 889,548, May 27, 1992, abandoned.

[51] Int. Cl.$^6$ .................................................. C08G 12/00
[52] U.S. Cl. ...................... 528/229; 528/230; 528/170; 528/220; 528/227; 528/228; 564/153
[58] Field of Search .......................... 564/153; 528/229, 528/230, 170, 220, 227, 228

[56] References Cited

U.S. PATENT DOCUMENTS

| | | | |
|---|---|---|---|
| 3,607,622 | 7/1968 | Espy | 162/167 |
| 4,293,693 | 10/1981 | Cohen et al. | 544/221 |
| 4,326,057 | 4/1982 | Cohen et al. | 544/221 |
| 4,447,594 | 5/1984 | Cohen et al. | 528/245 |
| 4,605,724 | 8/1986 | Ambrose et al. | 528/73 |
| 4,663,448 | 5/1987 | Chiu | 536/111 |
| 4,675,394 | 6/1987 | Solarek et al. | 536/43 |
| 4,703,116 | 10/1987 | Solarek et al. | 536/104 |
| 4,731,162 | 3/1988 | Solarek et al. | 162/175 |
| 4,741,804 | 5/1988 | Solarek et al. | 162/175 |
| 4,749,800 | 6/1988 | Jobe et al. | 549/452 |
| 4,788,280 | 11/1988 | Billmers et al. | 536/104 |
| 4,801,699 | 1/1989 | Jobe et al. | 536/59 |
| 4,804,769 | 2/1989 | Solarek et al. | 549/374 |
| 4,839,449 | 6/1989 | Billmers et al. | 526/238.2 |
| 4,866,151 | 9/1989 | Tsai et al. | 527/300 |
| 5,011,918 | 4/1991 | Bilmers et al. | 536/18.7 |
| 5,049,634 | 9/1991 | Tsai et al. | 527/312 |
| 5,386,040 | 1/1995 | Martino et al. | 568/483 |

FOREIGN PATENT DOCUMENTS 0366451  5/1990  European Pat. Off. ....... A61K 31/13

OTHER PUBLICATIONS

John D. Peabody, III., "Synthesis and Complexation Studies of Cyclohexane–based Tripondands", Thesis Dissertation, University of New Hampshire, pp. 11–12, (1990).
CA111(20):186242u, 1988.

*Primary Examiner*—Gary Geist
*Assistant Examiner*—Rosalynd Williams
*Attorney, Agent, or Firm*—Margaret B. Kelley

[57] ABSTRACT

Low molecular weight polyaldehydes are prepared by converting the acetal groups of the low molecular weight polyacetal to aldehyde groups or by reacting an aldehyde-containing reagent (e.g., glyoxal) with a polyamide.

8 Claims, No Drawings

LOW MOLECULAR WEIGHT POLYALDEHYDES

This is a division of application Ser. No. 08/310,451 filed on Sep. 22, 1994, now U.S. Pat. No. 5,466,862, which is a division of application Ser. No. 08/074,278 filed on Jun. 8, 1993, now U.S. Pat. No. 5,386,040, which is a continuation of application Ser. No. 07/889,548 filed May 27, 1992, now abandoned.

BACKGROUND OF THE INVENTION

The present invention relates to low molecular weight derivatives containing more than one aldehyde group. It also relates to the low molecular weight acetal derivatives used in the preparation thereof. It further relates to processes for introducing aldehyde groups into low molecular weight compounds.

There is a need for formaldehyde-free crosslinking agents (i.e., agents that do not release formaldehyde on crosslinking) particularly for use in durable press and corrugating adhesive applications.

U.S. Pat. No. 4,447,594 (issued May 8, 1984 to S. M. Cohen et al.) discloses polyaldehyde adducts of isocyanuric acid and acrolein. Preparation of these adducts is described in U.S. Pat. No. 4,326,057 (issued Apr. 20, 1982 to S. M. Cohen et al.). These adducts or their hemiacetals are used in heat-curable coating compositions containing a polyunsaturated ester of an ethylenically unsaturated acid (e.g., acrylic acid, methacrylic acid, or itaconic acid), a polyhydric alcohol, and a free radical or ionic initiator.

U.S. Pat. No. 4,293,693 (issued Oct. 6, 1981 to S. M. Cohen et al.) discloses isocyanuric aldehydes also referred to as (3-oxopropyl)isocyanurates, which have the formula

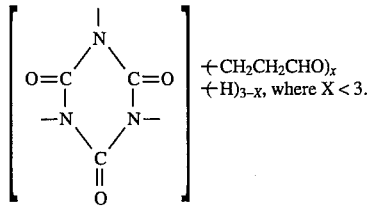

These polyaldehydes are used in the preparation of hemiacetals, which are themselves useful as polymerizing or crosslinking agents for polyfunctional compounds containing hemiacetal reactive groups (e.g., amines, amides, alcohols, thiols, and oxiranes).

SUMMARY OF THE INVENTION

Low molecular weight polyacetals are prepared by reacting an acetal-containing reagent with a polyfunctional compound such as a polyol, a polyamine, a polyester, or a polyhalide. As used herein, a polyfunctional compound is a compound containing two or more functional groups bonded to different carbon atoms. The acetal-containing reagent contains a functional group reactive with the functional groups of the polyfunctional compound (i.e., with the hydroxyl groups of the polyalcohol, the amine groups of the polyamine, the ester groups of the polyester, or the halide groups of the polyhalide). The linkages formed by these reactions will be an ether linkage, amine linkage, amide linkage, or quaternary ammonium linkage. When the quaternary ammonium linkage is present, a counter anion ($Y^-$) will be present. Typical acetal-containing reagents include dimethoxyethyl-chloracetamide, 2-ethylene-5,5-dimethyl-1,3-dioxane, N,N-bis-(diethoxyethyl) methyl amine, and aminoacetaldehyde dimethyl acetal.

The low molecular weight polyacetals have the general formula

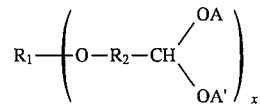

or

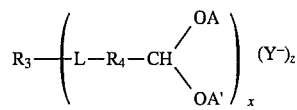

$R_1$ is the residue from a low molecular weight polyalcohol after reaction of the acetal-containing reagent's functional group with the alcohol groups of the polyalcohol; $R_2$ is a divalent organic group; A and A' are independently a lower alkyl group or A and A' together form at least a five-membered cyclic acetal; x is 2 to less than 20, preferably 2–10, most preferably 2–6; $R^3$ is the residue from a low molecular weight polyamine after reaction of the acetal-containing reagent's functional group with the amine groups of the polyamine, or the residue from a low molecular weight polyester after reaction of the acetal-containing reagent's functional group with the ester groups of the polyester, or the residue from a low molecular weight polyhalide after reaction of the acetal-containing reagent's functional group with the halide groups of the polyhalide; $R_4$ is a divalent organic group; L is $N(R_5)$ or $N^+(R_5)_2$; $R_5$ is hydrogen, a $C_1$–$C_{10}$, preferably $C_1$–$C_4$ alkyl or

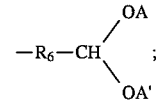

$R_6$ is a divalent organic group; $Y^-$, present when L is $N^+(R_5)_2$, is an anion; and z, if present, is equal to x. The molecular weight of the polyacetals ranges from about 200–3000, preferably about 250–1000.

Low molecular weight polyaldehydes are prepared (i) by hydrolyzing a low molecular weight polyacetal at a pH of about 3.0 or less or (ii) by reacting an aldehyde-containing reagent (e.g., glyoxal or glutaraldehyde) with a low molecular weight polyfunctional compound such as those described above. When the polyaldehydes are prepared by reacting an aldehyde-containing reagent with a low molecular weight polyfunctional compound, the aldehyde-containing reagent must contain a functional group reactive with the functional groups of the polyfunctional compound.

The low molecular weight polyaldehydes have the general formula $R_1$—(O—$R_2$—CHO)$_x$ or $R_3$—(L—$R_4$—CHO)$_x$ $(Y^-)_z$. $R_1$ to $R_4$, $R_6$, L, Y, x and z are as defined above and $R^5$ is (i) hydrogen or (ii) a $C_1$–$C_{10}$ alkyl, preferably a $C_1$–$C_4$ alkyl, or (iii) $R_6$—CHO. The molecular weight of the polyaldehydes ranges from about 200–3000, preferably about 250–1000.

The polyaldehydes are particularly useful as crosslinking agents because of their high reactive density (i.e., large number of reactive groups per molecular weight of the compound) and because they do not release formaldehyde on crosslinking. Applications for these products include durable press coatings, pressure sensitive adhesives, grocery bag adhesives, corrugating adhesives, paper wet-strength additives, non-woven binders, bonding resins, and molding resins.

The polyacetals are also useful as crosslinking agents for the same reasons, as well as the fact that they do not release formaldehyde on crosslinking. They react with various functional groups through transacetalization.

DESCRIPTION OF THE PREFERRED EMBODIMENTS

As used herein, the term "polyalcohol" is intended to refer to polyhydric alcohols having at least two hydroxyl groups bonded to different carbon atoms. Such polyalcohols include ethylene glycol, 1,2- or 1,3-propanediol, 1,2-butane-diol, 1,6- or 2,5-hexane-diol, 2,4- or 1,5-pentanediol, 2,4-heptanediol, 2-methyl-1,3- or 2,4-pentanediol, 2-ethyl-1,3-hexanediol, 2,2-dimethyl or 2,2-diethyl-1,3-propanediol, 1,2- or 1,4-cylcohexanediol, 1,4-bis(hydroxymethyl)cyclohexane, 2,2-diethyl-1,3-butanediol, 2-butene-1,4-diol, trimethylolpropane, trimethylolethane, glycerol, 1,2,4-butanetriol, 1,2, 6-hexanetriol, erythritol, D- or L-threitol, sorbitol, pentaerythritol, D-mannitol, diethylene glycol, triethylene glycol, dipropylene glycol, diglycerol, poly(tetramethylene ether) glycols, 2,2-bis(hydroxyethoxy-phenyl)propane, and 2,2-bis(hydroxypropoxy phenyl)propane.

The reaction of polyols such as sucrose, glycerol, and pentaerythritol (but not sorbitol) with N-2,2-dimethoxyethyl- N-methyl chloroacetamide (DMCA) can be carried out at 60°–85° C. in a solvent using sodium carbonate or preferably sodium hydride as the base. Reactions in water using sodium hydroxide or sodium carbonate as the base result in mostly hydrolyzed DMCA.

The alkoxides are formed first by slowly adding the sodium hydride to a mixture of polyol in solvent under nitrogen and, after the evolution of hydrogen ceases, the DMCA is added dropwise. Preferably, the reaction with glycerol and pentaerythritol is carried out at 60° C. in tetrahydrofuran using a phase transfer catalyst such as tricapryl methyl ammonium chloride and a 10% molar excess of both sodium hydride and N-2,2-dimethoxyethyl-N-methyl chloroacetamide. The products usually have hydroxyl functionality present (as shown by IR) and even the use of 100% molar excess of N-2,2-dimethoxyethyl-N-methyl chloracetamide does not give a product that is totally substituted. For example, gel permeation chromatography shows that the product prepared from pentaerythritol contains 2, 3, and 4 substitutions of N-2,2-dimethoxyethyl-N-methyl chloracetamide on the pentaerythritol. Preferably, the reaction with sucrose is carried out in dimethyl formamide using a hydroxyl to N-2,2-dimethoxyethyl-N-methyl chloroacetamide molar ratio of about 8 to 4 to about 8 to 6.

Suitable polyamines include hexamethylene diamine, ethylene diamine, phenylenediamine, toluenediamine, and the like. Polyamines such as ethylene diamine or 3,3'-diamino-N-methyl dipropylamine can be reacted with halide-containing acetals such as N-2,2-dimethoxyethyl-N-methyl chloroacetamide, chloroacetaldehyde dimethyl acetal, or bromoacetaldehyde dimethyl acetal under varying conditions (e.g., at 70°–90° C. for 4–72 hours) using different solvents (e.g., toluene/water or dimethylformamide) and various catalysts (e.g., sodium carbonate or sodium hydroxide).

Suitable polyesters include triethyl citrate, dimethyl adipate, dimethyl glutarate, and the like.

Suitable polyhalides include pentaeripthritol tetrabromide, 1,4-dichloro-butene, 1,4-dibromo-butene, and the like.

Polyesters and polyhalides can be reacted with amino acetals such as aminoacetaldehyde dimethyl acetal or N,N-bis(2,2-diethoxyethyl)methyl amine under varying conditions (e.g., at 60°–90° C. for 14–40 hours) using no solvent or different solvents (e.g., tetrahydrofuran or toluene) and no catalyst or various catalysts (sodium hydroxide or organic amines).

Polyaldehydes of low molecular weight can be prepared by hydrolyzing the above polyacetals at a pH below about 3.0.

It can be appreciated by the practitioner that a large number of variations may be effected in selecting the acetal and aldehyde-containing derivatizing reagents, reacting them with polyols, polyester, polyamines, or polyhalides, converting the acetal groups to aldehyde groups if an acetal-containing derivatizing reagent is used and an aldehyde-containing final product is desired, and utilizing the acetal- or aldehyde-containing derivatives as crosslinking agents in accordance with the procedures described above without materially departing from the scope and spirit of the invention. Such variations will be evident to those skilled in the art and are to be included within the scope of the invention.

In the examples which follow, all parts and percentages are given by weight and all temperatures are in degrees Celsius unless otherwise noted.

The amount of acetal groups (calculated as percentage aldehyde) was determined quantitatively by titration. The quantitative test is carried out by slurrying 5.0 g. of polyacetal in sufficient distilled water to give 500 g. The pH is adjusted to 2.5 with hydrochloric acid. A 100 g. portion of the dispersed or solubilized polyacetal is weighed out, titrated with 0.1 NaOH to the first end point (inflection point is between pH 4.0 and 5) and the ml. of NaOH required is recorded ($T_1$). An aqueous solution (50 ml.) of hydroxylamine hydrochloride (prepared by dissolving 34.75 g. in a 1000 ml. volumetric flask and diluting to the mark) is added to a 100 g. portion of the dispersed or solubilized polyacetal, heated at reflux for 60 minutes, and titrated with 0.1N NaOH to pH 4.5. The ml. of NaOH required to reach the inflection point (pH 3.0–3.5) is recorded ($T_2$). Best results are obtained using an automatic titrator.

$$\% \text{ aldehyde} = \frac{(T_2 - T_1) \times (\text{normally of NaOH}) \times (2.9)}{\text{polyacetal weight*}}$$

\* Polyacetal weight = 100 g. × % solids of dispersed polyacetal.

Example 1

This example describes the preparation of polyacetals by the reaction of the polyols glycerol, pentaerthyritol, and sucrose with the acetal-containing reagent N-2,2-dimethoxyethyl-N-methyl chloroacetamide (DMCA).

Part A—Reaction With Glycerol

The polyacetal has the formula

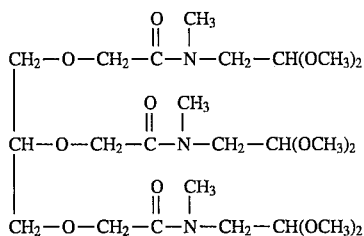

In a 4-necked, 500 ml. round bottom flask equipped with a mechanical stirrer, nitrogen inlet, addition flask, thermometer and reflux condenser were mixed 15 g. (0.155 moles) of glycerol, 60 g. of tetrahydrofuran (THF), and 1.0 g. tricaprylmethyl ammonium chloride (a phase transfer catalyst) with vigorous stirring. Then 12.26 g. (0.511 moles—10% excess) of sodium hydride (NaH) was added slowly. During the addition, the temperature was raised to 57°–60° C. (reflux) to prevent clumping. The reaction mixture was held for 1 hour after the sodium hydride addition was complete. Then 99.9 g. (0.511 moles—10% excess) of 100% active DMCA was added dropwise while maintaining the reaction temperature at 57°–60° C. Progress of the reaction was followed by working up aliquots of the reaction mixture and monitoring the disappearance of DMCA by gas chromatography or by ionic chlorine titration. When the reaction was complete (after about 20.0 hrs.), the salts were filtered off and the solvent was evaporated off. The product was purified by dissolving it in 40 ml. of methanol, extracting it with petroleum ether, and evaporating the methanol under reduced pressure. Inorganic chlorine titration showed 100% reaction; gas chromatography showed 95% reaction efficiency. The product was useful as a corrugating adhesive additive.

Part B—Reaction With Pentaerythritol

The polyacetal has the formula

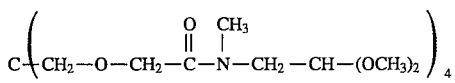

The reagents and amounts used were as follows: 15 g. (0.11 moles) pentaerythritol; 110 g. THF; 1.0 g. tricaprylmethyl ammonium chloride; 11.6 g. (0.48 moles) NaH; and 94.6 g. (0.48 moles) DMCA. The procedure of Example 1 was followed. Inorganic chlorine titration showed 100% reaction; gas chromatography showed 90% reaction efficiency. The product was useful as a corrugating adhesive additive.

Part C—Reaction with Sucrose

The reagents and amounts used were as follows: 20.0 g. (0.06 moles) sucrose; 110 g. DMF; 6.4 g. (0.26 moles) NaH; and 47.0 g. (0.24 moles) DMCA. The procedure of Example 1 was followed except that the reaction temperature was maintained at 100° C. during the dropwise addition of the DMCA and, after the reaction was complete (about 24 hrs.), the solution was filtered and the dimethyl formamide evaporated off under vacuum at 45° C. for 3.5 hours. Inorganic chlorine titration showed 85% reaction efficiency.

Example 2

This example describes the preparation of cyclic polyacetals by the reaction of the polyols glycerol, pentaerythritol, and sorbitol with 2-ethenyl-5,5-dimethyl-1,3-dioxane (EDD).

Part A—Reaction with Glycerol

The polyacetal has the formula

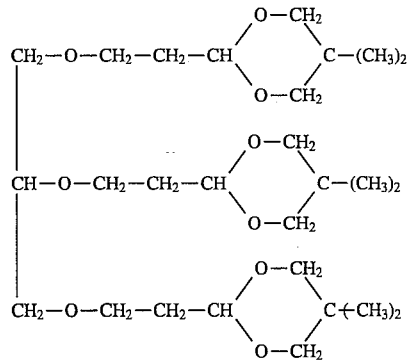

In a 3-neck 100 ml. round bottom flask equipped with a mechanical stirrer, nitrogen inlet, thermometer, and reflux condenser were mixed 5.0 g. (0.051 moles) of glycerol and 23.9 g. (0.168 moles) of EDD. To the stirred solution was added 0.1 g. (0.005 moles) of p-toluene sulfonic acid. The mixture was heated to 100° C. The disappearance of EDD was followed by gas chromatography to determine the end of the reaction (about 6.5 hours). When complete, the reaction mixture was cooled and diluted with 20 g. of methylene chloride, 10 g. of sodium carbonate was added to neutralize the excess acid and the mixture was stirred for 1.0 hour. The salts were filtered off and the solvent was stripped off at 45° C. under reduced pressure for 1.5 hours. Gas chromatography showed 100% reaction efficiency.

Part B—Reaction with Pentaerythritol

The polyacetal has the formula

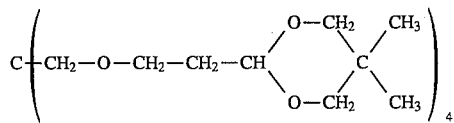

The procedure of Part A was followed except that the reaction was run at 110° C. for 4.0 hours using 2.0 g. (0.0147 moles) pentaerythritol, 9.25 g. (0.065 moles) EDD, and 0.049 g. (0.00025 moles) p-toluene sulfonic acid. Gas chromatography showed 100% reaction efficiency.

Part C—Reaction with Sorbitol

The polyacetal has the formula

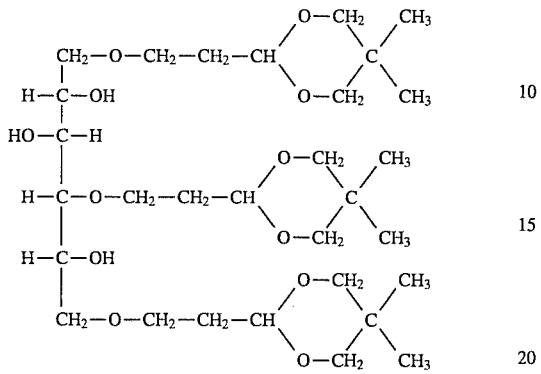

The procedure of Part A was followed except that the temperature was 95° C. and the molar ratio of sorbitol to EDD was 1:3.

Example 3

This example describes the preparation of a cyclic polyacetal by the reaction of the polyamines N,N,N',N'-tetrakis (2-hydroxyethyl) ethylene diamine and 2,2-bis(hydroxymethyl)-2,2',2"-nitrilotriethanol with EDD.

Part A—Reaction with N,N,N',N' Tetrakis (2-hydroxyethyl) Ethylene Diamine (TKHED)

The polyacetal has the formula

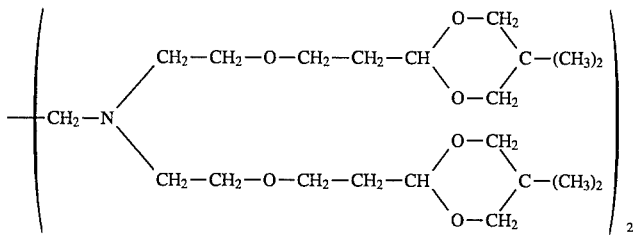

The reaction was carried out using the procedure of Example 3 except that the reaction was run for 1 hour using 6.0 g. (0.025 moles) TKHED, 15.9 g. (0.111 moles) EDD, and 9.6 g. (0.0504 moles) p-toluene sulfonic acid. Neutralization was done in methanol as a solvent. Gas chromatographic analysis showed 100% reaction efficiency.

Part B—Reaction with 2,2-Bis(hydroxymethyl)-2,2',2"-Nitrilotriethanol (BHMNTE)

The polyacetal has the formula

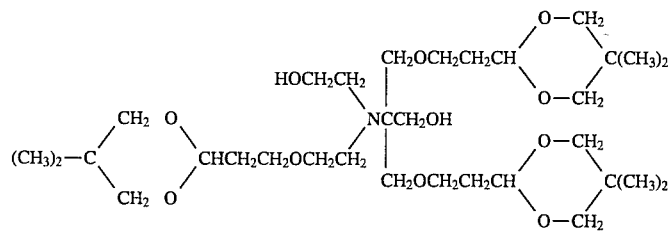

The reaction was carried out using the procedure of Example 3 except that the reaction was run for 25 hours at 110° C. using 5.0 g. (0.024 moles) BHMNTE, 11.2 g. (0.079 moles) EDD, and 4.45 g. (0.023 moles) p-toluene sulfonic acid. The p-toluene sulfonic acid was added in increments over the 25 hour reaction time. Neutralization was done in methanol as solvent. Gas chromatographic analysis showed 100% reaction efficiency.

Example 4

This examples describes the preparation of polyacetals by the reaction of the polyamines 3,3'-diamino-N-methyl dipropylamine and ethylene diamine with DMCA.

Part A—Reaction with 3,3'-Diamino-N-Methyl Dipropylamine (DAMDA)

The polyacetal has the formula

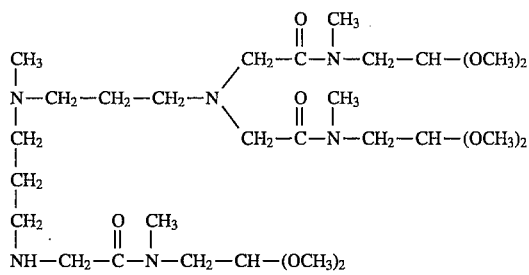

In a 4-necked, 250 ml. round bottom flask equipped with a mechanical stirrer, nitrogen inlet, addition flask, thermometer, and reflux condenser were mixed 70.0 g. of water, 30.0 g. of toluene, 43.0 g. (0.408 moles) of sodium carbonate, and 19.75 g. (0.136 moles) of DAMDA. The reaction mixture was heated to 70° C. with vigorous stirring and 79.74 g. (0.408 moles) of DMCA were added dropwise. Completion of the reaction (about 26 hours) was monitored by gas chromatography or ionic chlorine titration. The product was recovered by filtering the solution, separating the water layer, removing the water at 50° C. under reduced pressure for 4.0 hours. The product was dissolved in methanol and filtered to remove the last of the salts. The methanol was then removed at 50° C. under reduced pressure for 1.0 hour. The product was dissolved in acetone, magnesium sulfate was added to dry the product. The mixture was allowed to stir overnight, filtered, and the acetone stripped off at 50° C. under reduced pressure for 3 hours. Inorganic chlorine and gas chromatographic analysis showed 97% reaction.

Part B—Reaction with Ethylene Diamine (EDA)

When the molar ratio of EDA to DMCA is 1:4, the polyacetal has the formula

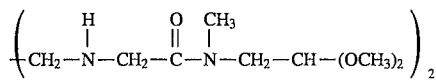

When the molar ratio of EDA to DMCA is 1:2, the polyacetal has the formula $$\left(-CH_2-N-CH_2-\overset{O}{\overset{\|}{C}}-N-CH_2-CH-(OCH_3)_2\right)_2$$
(with H on first N, CH₃ on second N)

The reaction was carried out using the procedure of Part A. The reagents and amounts used were 60 g. of water, 40 g. of toluene, 25.4 g. (0.4 moles) of sodium carbonate, 6.0 g. (0.11 moles) of EDA, and 79.18 g. (0.4 moles) of DMCA. The reaction time was about 4.5 hours. Inorganic chlorine and gas chromatographic analysis showed 100% reaction.

Example 5

This example describes the preparation of a polyacetal from the polyamine ethylene diamine (EDA) and bromoacetaldehyde dimethyl acetal (BADMA).

In a 4-neck, 250 ml. round bottom flask equipped with a reflux condenser, nitrogen inlet, thermometer, addition funnel, and mechanical stirrer were mixed 50 g. of toluene, 50 g. of 20% aqueous NaOH, and 2.0 g. (0.034 moles) of ethylene diamine. The reaction mixture was heated to 80°–85° C. and 22.5 g. (0.133 moles) BADMA was slowly added while maintaining the temperature constant. The reaction mixture was stirred for 72 hours. The aqueous layer was removed, and the toluene and unreacted starting materials evaporated off from the organic layer to isolate the product as a brown oil soluble in water and toluene. Inorganic bromine titration and gas chromatography showed 80% reaction efficiency.

Example 6

This example describes the preparation of polyacetals by the reaction of polyamines DAMDA and EDA with the polyhalide pentaerythrityl tetrabromide and 1,4-dibromo-2-butene.

Part A—Reaction With Pentaerythrityl Tetrabromide

The polyacetal has the formula

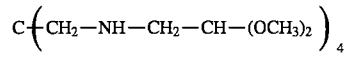

In a 3-necked, 50 ml. round bottom flask equipped with a mechanical stirrer, thermometer, and nitrogen inlet were mixed 7.7 g. (0.02 moles) of pentaerythrityl tetrabromide and 16.8 g. (0.016 moles) of aminoacetaldehyde dimethyl acetal. The reaction mixture was heated to 90° C. with stirring and filtered. The product was washed with tetrahydrofuran to give white crystals having a melting point of 115°–119° C. Inorganic bromine titration indicated 98% reaction efficiency after 23 hours. Gas chromatographic analysis showed 90% reaction efficiency. Nitrogen analysis showed 90.4% efficiency. Similar reactions using dimethyl aminoacetaldehyde dimethyl acetal showed poor reaction efficiencies (5–6%).

Part B—Reaction With 1,4-Dibromo-2-Butene

The polyacetal has the formula

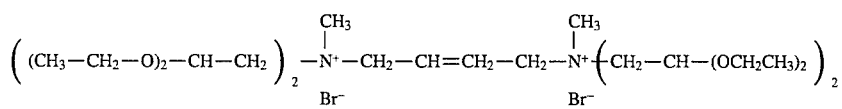

In a 3-necked, 100 ml. round bottom flask equipped with a mechanical stirrer, nitrogen inlet, addition flask, thermometer, and reflux condenser were mixed 12.35 g. (0.047 moles) of N,N-bis (2,2-diethoxyethyl)methyl amine and 22 g. of tetrahydrofuran. While stirring at room temperature 5.0 g. (0.023 moles of 1,4-dibromo-2-butene was slowly added while maintaining the temperature. After the addition was complete, the temperature was raised to reflux (60° C). The reaction was complete after about 14 hours according to inorganic Br⁻ titration. The white solid product was filtered off and then washed with tetrahydrofuran. Gas chromatographic analysis and ionic bromine titration showed 90% reaction efficiency. Nitrogen analysis indicated 78% reaction efficiency.

Similar reactions using 1,4-dichloro-2-butene instead of 1,4-dibromo-2-butene gave poor reaction efficiencies (5%).

Example 7

This example describes the preparation of a polyacetal from the polyester triethyl citrate and aminoacetaldehyde dimethyl acetal (AADMA). The polyacetal has the formula

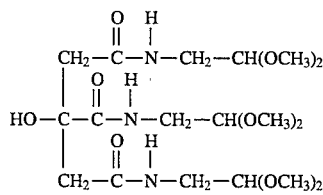

In a 500 ml., 4-necked round bottom flask equipped with a mechanical stirrer, nitrogen inlet, thermometer, reflux condenser and Dean Stark trap were mixed 69.1 g. (0.25 moles) of triethyl citrate, 157.7 g. (1.5 moles) of AADMA, and 0.06 g. (0.0015 moles) of freshly ground sodium hydroxide. The reaction mixture was heated under nitrogen with good mixing to 90° C. The reaction, which was followed by infrared spectroscopy and/or gas chromatography, usually took 35–40 hours. After the reaction was complete, excess AADMA was stripped off at 70° C. under vacuum for 3.0 hours. The product was a water-soluble, viscous light brown oil which crystallized to a hard wax over 5 to 10 days. Gas chromatography showed the reaction efficiency was greater than 97%.

Example 8

This example describes the preparation of a polyketal/polyacetal. The polyester triethyl citrate and furfuryl amine were reacted to give a polyfuran which was then reacted with bromine and methanol to give the polyketal/acetal which has the formula

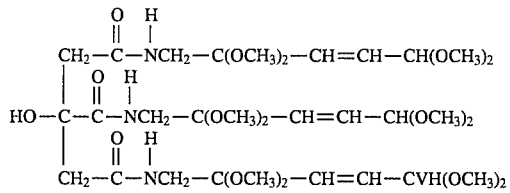

In a 250 ml., 4- necked round bottom flask equipped with a mechanical stirrer, nitrogen inlet, thermometer, reflux condenser and Dean Stark trap were mixed 30 g. (0.11 moles) of triethyl citrate and 64.1 g. (0.66 moles) of furfuryl amine (100% excess) and heated to 90° C. Then 0.04 g. (0.001 moles) of freshly ground sodium hydroxide were added. The ethanol was removed as it was formed. The reaction was finished in 30 to 40 hours. The reaction mixture was cooled, dissolved in 120 ml. acetone and then precipitated in 2 l. of petroleum ether to give 41.3 g. of a light tan product. Gas chromatography showed the reaction efficiency to be 100%. The resulting polyfuran was reacted with bromine and methanol at –30° C. to give the polyketal/acetal as a viscous brown syrup.

Example 9

This example describes the preparation of polyaldehydes by the hydrolysis of the polyacetals of Example 1—Part A, Example 1—Part B, and Example 4—Part B.

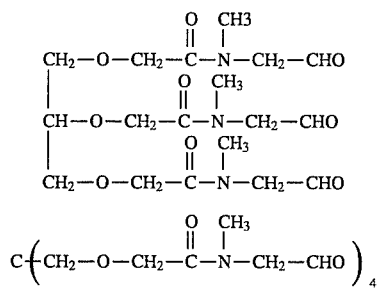

When the molar ratio of EDA to DMCA is 1:2 and 1:4, the polyaldehydes have the formulas

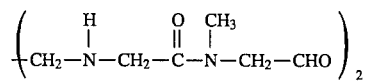

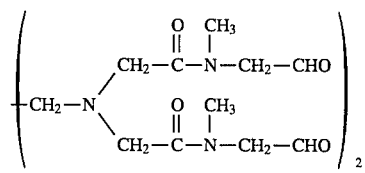

Part A

The hydrolysis of the polyacetals of Example 1, Parts A and B, was carried out by mixing 8 g. of the polyacetal, 100 g. of tetrahydrofuran, 30 g. of water, and 8 g. of Amberlyst 15 (a macroreticular sulfonic acid based polystyrene cation exchange resin available from Rohm & Haas). The reaction mixture was stirred at room temperature overnight and then at 55° C. for 7.0 hours. The product was isolated by filtering off the Amberlyst 15 and evaporating off the solvent under vacuum. A 0.5% aqueous solution was prepared, adjusted to pH 2.3, and 50 ml. of 0.5M hydroxylamine was added. The mixture was refluxed for 45 minutes, cooled, and titrated with 0.1N sodium hydroxide.

Part B

The hydrolysis of the polyacetals was carried out by preparing 100 g. of a 0.5% solution of the polyacetal in water and heating the solution (pH adjusted to 1.5–2.0) for 20 minutes at 100° C. The reaction mixture was cooled, adjusted to pH 2.3 with hydrochloric acid, and 50 ml. of 0.5M hydroxylamine hydrochloride were added. The mixture was refluxed for 45 minutes, cooled, and titrated with 0.1N sodium hydroxide.

The above polyaldehydes were used as crosslinking agents for the butyl acrylate/butyl nitrile/acrylic acid polymers used in pressure sensitive adhesives.

Example 10

This example describes the direct preparation of a polyaldehyde having the formula

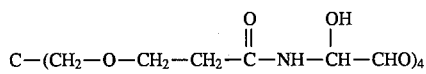

$$C-(CH_2-O-CH_2-CH_2-\overset{O}{\overset{\|}{C}}-NH-\overset{OH}{\overset{|}{CH}}-CHO)_4$$

by the reaction of glyoxal with the polyamide tetra-(amidoethoxy)tetramethyl methane (TATM). The TATM can be prepared by reacting pentaerythritol with acrylamide.

In a 250 ml., 4-neck round bottom flask equipped with a mechanical stirrer, nitrogen inlet, thermometer, and reflux condenser were mixed 10 g. (0.024 moles) of TATM, 100 g. of water, and 15.2 g. (0.105 moles) of 40% aqueous glyoxal. The pH was adjusted to 7.4 with dibasic sodium phosphate (10% aqueous solution). The mixture was heated to 40° C. and reacted for 30 hours. The pH was then adjusted to 3.5 with aqueous hydrochloric acid to stop the reaction. The product was stored as a 10% aqueous solution (pH=4.0).

In summary, the present invention is seen to provide compounds having a high aldehyde or acetal density in low molecular weight reagents. The compounds are particularly useful as crosslinking agents.

Now that the preferred embodiments of the invention have been described in detail, various modifications and improvements thereon will become readily apparent to those skilled in the art. Accordingly, the spirit and scope of the present invention are to be limited only by the appended claims and not by the foregoing specification.

What is claimed:

1. A polyaldehyde having a molecular weight of about 200–3000 and the general structure $R_3-(L-R_4-CHO)_x(Y)_z$, wherein $R_3$ is the residue from a polyamine containing at least two amine groups bonded to different carbon atoms or the residue from a polyhalide containing at least two halide groups bonded to different carbon atoms; $R_4$ is a divalent organic group; L is $N(R_5)$ or $N^+(R_5)_2$; $R_5$ is hydrogen, a $C_1$–$C_{10}$ alkyl group or $-R_6-CHO$; $R_6$ is a divalent organic group; Y is an anion which is present when L is $N^+(R_5)_2$; x is 2 to less than 20; and z, if present, is equal to x.

2. The polyaldehyde of claim 1, wherein the polyamine is 3,3'-diamino-N-methyl dipropylamine or ethylene diamine.

3. A polyaldehyde having a molecular weight of about 200–3000 and the general structure $R_3-(L-R_4-CHO)_x(Y)_z$, wherein $R_3$ is the residue from pentaerythrityl tetrabromide or 1,4-dibromo-2-butene; $R_4$ is a divalent organic group; L is $N(R_5)$ or $N^+(R_5)_2$; $R_5$ is hydrogen, a $C_1$–$C_{10}$ alkyl group or $-R_6-CHO$; $R_6$ is a divalent organic group; Y is an anion which is present when L is $N^+(R_5)_2$; x is 2 to less than 20; and z, if present, is equal to x.

4. The polyaldehyde of claim 1, which is prepared by reacting ethylene diamine with N-2,2-dimethoxyethyl-N-methyl chloroacetamide to form a polyacetal and then hydrolyzing the polyacetal to the polyaldehyde.

5. The polyaldehyde of claim 1, wherein the molecular weight of the polyaldehyde is about 250–1000.

6. A polyaldehyde which is prepared by (a) reacting (i) a polyamine containing at least two amine groups bonded to different carbon atoms or a polyhalide containing at least two halide groups bonded to different carbon atoms and (ii) an acetal-containing reagent containing a functional group reactive with the amine or halide groups to form a polyacetal having a molecular weight of about 200–3000 and (b) hydrolyzing the polyacetal to the polyaldehyde which has the general structure $R_3-(L-R_4-CHO)_x(Y)_z$, wherein $R_3$ is the residue from pentaerythrityl tetrabromide or 1,4-dibromo-2-butene; $R_4$ is a divalent organic group; L is $N(R_5)$ or $N^+(R_5)_2$; $R_5$ is hydrogen, a $C_1$–$C_{10}$ alkyl group or $-R_6-CHO$; $R_6$ is a divalent organic group; Y is an anion which is present when L is $N^+(R_5)_2$; x is 2 to less than 20; and z, if present, is equal to x.

7. The polyaldehyde of claim 6, wherein the polyamine is hexamethylene diamine, ethylene diamine, phenylene diamine, toluene diamine, or 3',3'-diamino-N-methyl dipropylamine.

8. The polyaldehyde of claim 6, wherein the molecular weight of the polyaldehyde is about 250–1000.

* * * * *